United States Patent [19]
Bono

[11] Patent Number: 5,954,722
[45] Date of Patent: Sep. 21, 1999

[54] POLYAXIAL LOCKING PLATE

[75] Inventor: Frank S. Bono, Leesburg, Ind.

[73] Assignee: DePuy Acromed, Inc., Cleveland, Ohio

[21] Appl. No.: 08/902,061

[22] Filed: Jul. 29, 1997

[51] Int. Cl.⁶ .................................................. A61B 17/56
[52] U.S. Cl. .............................................. 606/61; 606/70
[58] Field of Search ................................. 606/69, 70, 71, 606/61, 60, 72, 73

[56] References Cited

U.S. PATENT DOCUMENTS

| | | |
|---|---|---|
| 4,484,570 | 11/1984 | Sutter et al. . |
| 5,053,036 | 10/1991 | Perren et al. ............................. 606/69 |
| 5,057,111 | 10/1991 | Park et al. ................................ 606/69 |
| 5,151,103 | 9/1992 | Tepic et al. .............................. 606/69 |
| 5,364,399 | 11/1994 | Lowery et al. . |
| 5,423,826 | 6/1995 | Coates et al. . |
| 5,520,690 | 5/1996 | Errico et al. ............................. 606/69 |
| 5,591,166 | 1/1997 | Bernhardt et al. ....................... 606/61 |
| 5,607,426 | 3/1997 | Ralph et al. . |
| 5,643,265 | 7/1997 | Errico et al. ............................. 606/70 |
| 5,735,853 | 4/1998 | Olerud ..................................... 606/71 |

OTHER PUBLICATIONS

"Aline™ Anterior Cervical Plating System", Smith & Nephew Orthopaedics, 7148–0203.

Primary Examiner—Guy V. Tucker
Attorney, Agent, or Firm—Barnes & Thornburg

[57] ABSTRACT

A locking plate apparatus for engagement with a bone is provided in accordance with the present invention. Locking plate apparatus includes a plate that has a body portion and an internal wall defining a plate hole through body portion and a bushing with a passageway therethrough. Bushing is sized for polyaxial rotation within plate hole. Locking plate apparatus also includes an attachment component that has a leading portion sized for extension through passageway and into bone and an opposite trailing portion. Trailing portion presses bushing against internal wall of plate to form a friction lock between bushing and plate in a selected polyaxial position.

28 Claims, 5 Drawing Sheets

POLYAXIAL LOCKING PLATE

BACKGROUND SUMMARY OF THE INVENTION

The present invention relates to a bone locking plate, more particularly the present invention relates to a bone locking plate that includes an adjustable attachment component. Most particularly, the present invention relates to a bone locking plate that includes an attachment component whose angle relative to the locking plate may be manipulated during surgery so that it extends into the bone in a desirable orientation.

The spinal column includes over twenty bones that are coupled together. These bones are capable of twisting and curving in a variety of directions relative to one another. Traumas and developmental irregularities can result, however, in spinal pathologies for which permanent immobilization of multiple vertebrae in the spinal column is required. It is known to place a bone screw through a bone plate along an axis that has been selected by the manufacturer of the plate. See for Example U.S. Pat. No. 5,364,399, entitled "Anterior Cervical Plating System", to Lowery et al. and U.S. Pat. No. 4,484,570, entitled "Device Comprising an Implant and Screws for Fastening Said Implant to a Bone, and a Device for Connecting Two Separated Pieces of Bone", to Sutter et al. Since bone screws are known to pull out of the bone over time, these conventional bone plates have main bone-plate screws that lock down using additional loose components that either cover adjacent screws or are threaded into the head/shaft of the bone screw to prevent the screws from backing out of the bone. Often, however, the most desirable screw angle for fixing the bone screw is difficult if not impossible to determine prior to surgery.

Therefore, conventional devices have been provided that allow the user to angulate a bone screw prior to placement. See U.S. Pat. No. 5,607,426, entitled "Threaded Polyaxial Locking Screw Plate Assembly" to Ralph et al. These conventional systems, however, also include multiple loose components that must be assembled to couple the bone screw head and plate hole bearing surface. These multi-component traditional plate assemblies can be cumbersome and tedious to manipulate during surgery to achieve the most desirable angle for directing the bone screw into the patient.

What is needed is a locking plate assembly that permits polyaxial coupling of the bone screw to the locking plate and that allows high angulation as well as rigid locking plate with fewer loose pieces.

According to the present invention, a locking plate apparatus suitable for engagement with a bone is provided. The locking apparatus includes a plate with a body portion and an internal wall defining a plate hole therethrough and an expandable bushing including a radially exterior surface and an opposite interior surface defining a passageway. The exterior surface of the bushing is sized to permit rotation of the bushing about a plurality of axes within the plate hole. In addition, the locking apparatus includes an attachment component with a leading portion sized for extension through the passageway and into the bone and an opposite leading portion sized to press the bushing against the internal wall of the plate to form a friction lock between the bushing and the plate.

According to another embodiment of the present invention a locking plate apparatus is provided that is suitable for attachment with a bone. The locking plate apparatus includes a plate that has a proximal surface, a distal surface, and an internal wall that defines a plate hole extending between the proximal and distal surfaces, an expandable bushing, and an attachment component sized for extension through the bushing. The bushing includes a radially exterior surface and an opposite interior surface defining a passageway. The exterior surface is sized for insertion into the plate hole of the plate and for engagement with the internal wall to couple movably the bushing to the plate. In addition, the attachment component includes a leading portion and an opposite leading portion. The leading portion has a tapered portion that diverges away from the leading portion and is sized for pressing the bushing toward the internal wall of the plate to form a friction lock between the bushing and the plate.

Still further, in accordance with the present invention a method for coupling two bone portions together is provided. The method includes the steps of providing a locking apparatus that includes a plate having a body portion and an internal wall defining at least two plate holes through the body portion, at least two expandable bushings press fit into the respective plate holes each having a radially exterior surface and an opposite interior surface and a first end and an opposite second end defining a passageway therebetween and at least two attachment components being sized for extension into the passageway, each attachment component including opposite leading and trailing portions. In addition, the method includes the steps of positioning the body portion upon the bone portions so that the plate holes in the plate are situated over bone, rotating at least one of the bushings within the plate hole about a plurality of axes until the first and second ends of the bushing are aligned along an axis that extends through a predetermined portion of the bone. Further, the method includes the steps of inserting the leading portion of one attachment component through each passageway and driving the trailing portion of each attachment component through the respective passageway until the leading portion is positioned in the bone and the exterior surface of the bushing is pressed against the internal wall of the plate to form a friction lock therebetween.

In yet another embodiment of the present invention, a bone fixation apparatus is provided that includes a plate with a plate hole through the plate, a bone fixation screw for extension through the plate hole and into a bone, and an expansion bushing carried in the plate hole. The bushing is threaded to engage the screw and expandable by the screw frictionally to lock in position in the plate hole.

In still another embodiment of the present invention, a plate for bridging between and fixing the relative portions of bones is provided. The plate includes plate holes adjacent each bone, each plate hole carrying an expandable bushing therein for swivel movement selectively to position the axis of the bushing relative to the adjacent bone and a bone screw for penetration into the bone and expanding the bushing to lock the bushing in a selected position in the plate.

Further, according to the present invention, a plate and screw apparatus for orthopaedic applications is provided that includes a plate with a plurality of plate holes formed therein, each plate hole having an internal wall, a radially expandable bushing positioned in each plate hole to be held by said internal wall, and a screw for each plate hole, each screw having a leading portion for engaging the bushing and a trailing portion for expanding the bushing into locking engagement with the internal wall.

Additional objects, features, and advantages of the invention will become apparent to those skilled in the art upon consideration of the following detailed description of the preferred embodiment exemplifying the best mode of carrying out the invention as presently perceived.

DETAILED DESCRIPTION OF THE DRAWINGS

Figure 1:
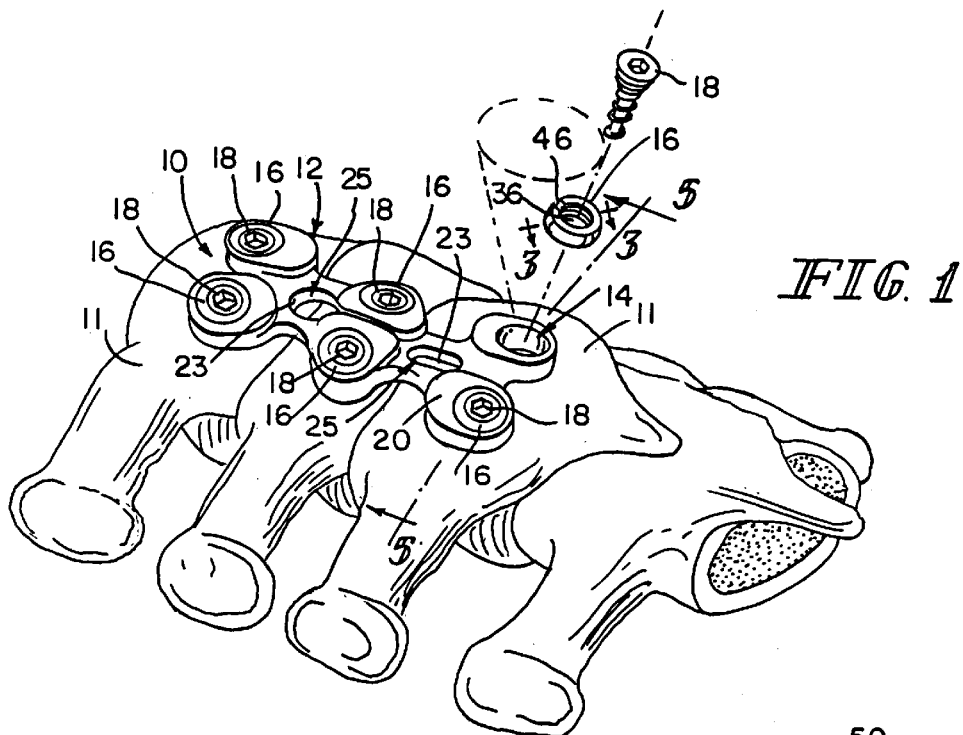
FIG. 1 is a perspective view of a locking apparatus in accordance with the present invention coupled to vertebrae and showing the locking apparatus including a locking plate having six plate holes and corresponding slotted bushings having a threaded passageway therethrough and thread-through bone screws.

FIG. 1 illustrates a locking plate apparatus 10 in accordance with the present invention as apparatus 10 appears to a surgeon during attachment of apparatus 10 to vertebrae 11. Locking plate apparatus 10 includes a locking plate 12 and corresponding semi-split donut shaped bushings 16 press-fit into locking plate 12 to form a plate subassembly 17, and thread-through bone screws 18. Locking plate apparatus 10 beneficially enables a surgeon, without a large number of loose pieces, to achieve infinite angulation (3-D) within a specified conical volume while rigidly locking bone screws 18 to rigid locking plate 12. Non-limiting examples of applications of locking plate apparatus 10 include the following: long bone fracture fixation/stabilization, small bone stabilization, lumbar spine as well as thoracic stabilization/fusion and burst fracture fixation, cervical spine compression/fixation, and skull fracture/reconstruction plating.

Figure 2:
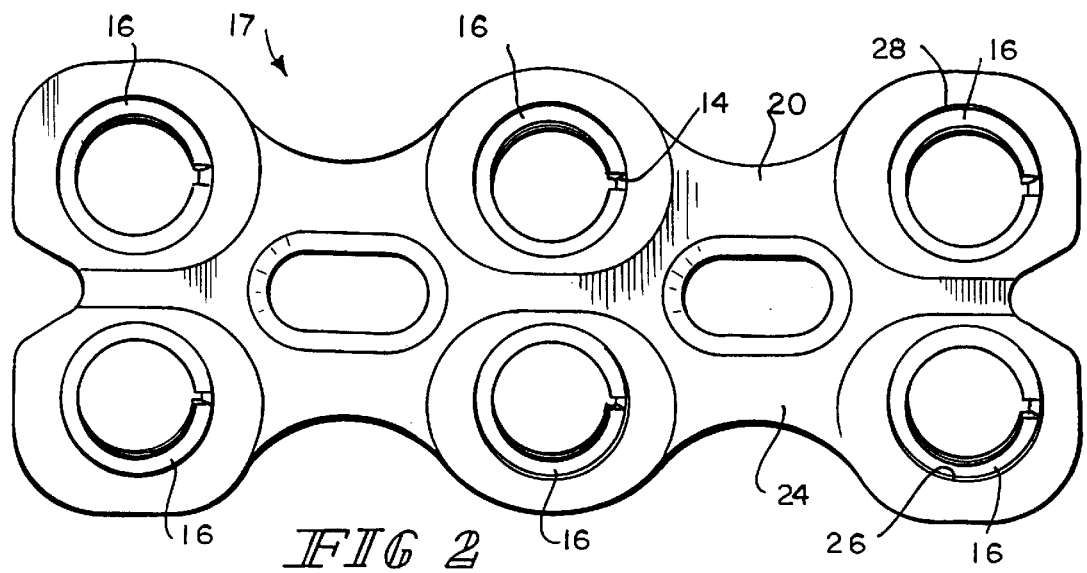
FIG. 2 is a top view of the locking apparatus of FIG. 1 prior to placement of the bone screws therethrough and showing six bushings press-fit into the six plate holes to form a locking plate/bushing subassembly.

Locking plate 12 includes a rigid body portion 20 having a proximal surface 22 resting upon vertebrae 11 and an opposite distal surface 24. In addition, body portion 20 includes two walls 23 that define two graft holes 25 and six internal walls 26 that define six spherically-shaped plate holes 14. Walls 23 may form graft holes 25 with a cylindrical, spherical shape, or any number of shapes. As shown in FIG. 2, each plate hole 14 is sized to receive bushing 16 therein to form subassembly 17. It is understood that plate holes 14 can also be elliptical-shaped, teardrop-shaped, or be defined by any number of rounded shapes in accordance with the present invention. Plate holes 14 extend through body portion 20 between proximal and distal surfaces 22, 24. As shown in FIGS. 1 and 2, three sets of two plate holes 14 are positioned to lie in a side-by-side relationship through body portion 20. Locking plate 12, however, may include one, two, four or five sets of two plate holes, or may be used in conjunction with any number of holes in a variety of plates. Although locking plate 12 is illustrated and described, it is understood that locking plates may be formed in any number of shapes and sizes for varying applications. Locking plate 12 is constructed of a titanium alloy, although it is understood that locking plate 12 may be constructed of titanium, stainless steel, or any number of a wide variety of materials possessing the mechanical properties suitable for coupling bones together.

As shown in FIG. 2, each donut-shaped bushing 16 is sized so that it is press fit into plate hole 14 of locking plate 12 to form subassembly 17. Bushing 16 will withstand pressure that is applied thereto without slipping out from plate holes 14 in locking plate 12. It is understood that while one bushing 16 will be described hereafter, the description applies to all bushings 16. Bushing 16 is constructed of a titanium alloy, although it is understood that bushing may be constructed of titanium, stainless steel, or any number of a wide variety of materials possessing the mechanical properties suitable for frictionally engaging locking plate 12.

Figure 3:
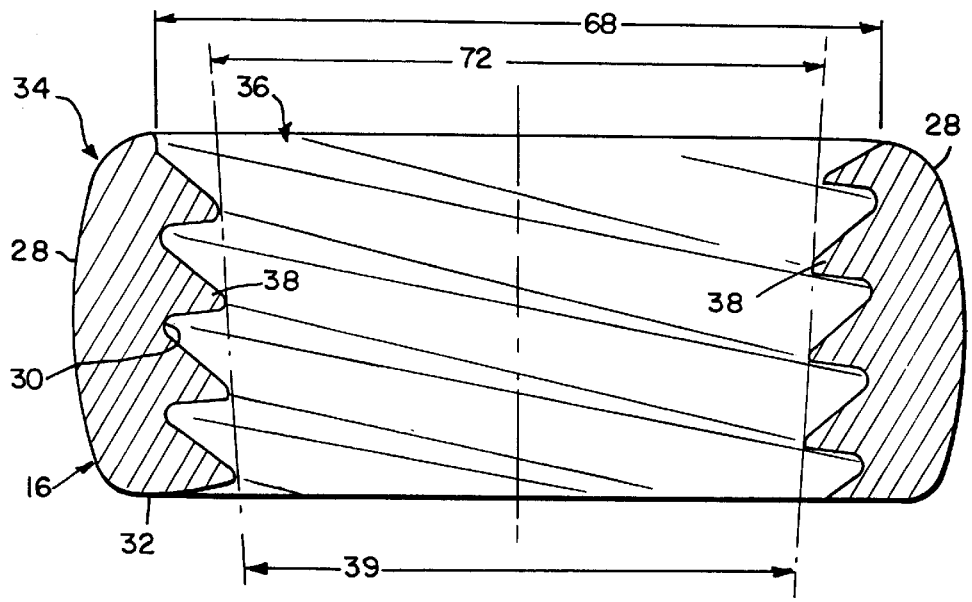
FIG. 3 is a cross sectional view taken along lines 3—3 of FIG. 1 showing the bushing having a cylindrically-shaped exterior surface and an interior surface having threads extending into the passageway.
Figure 5:
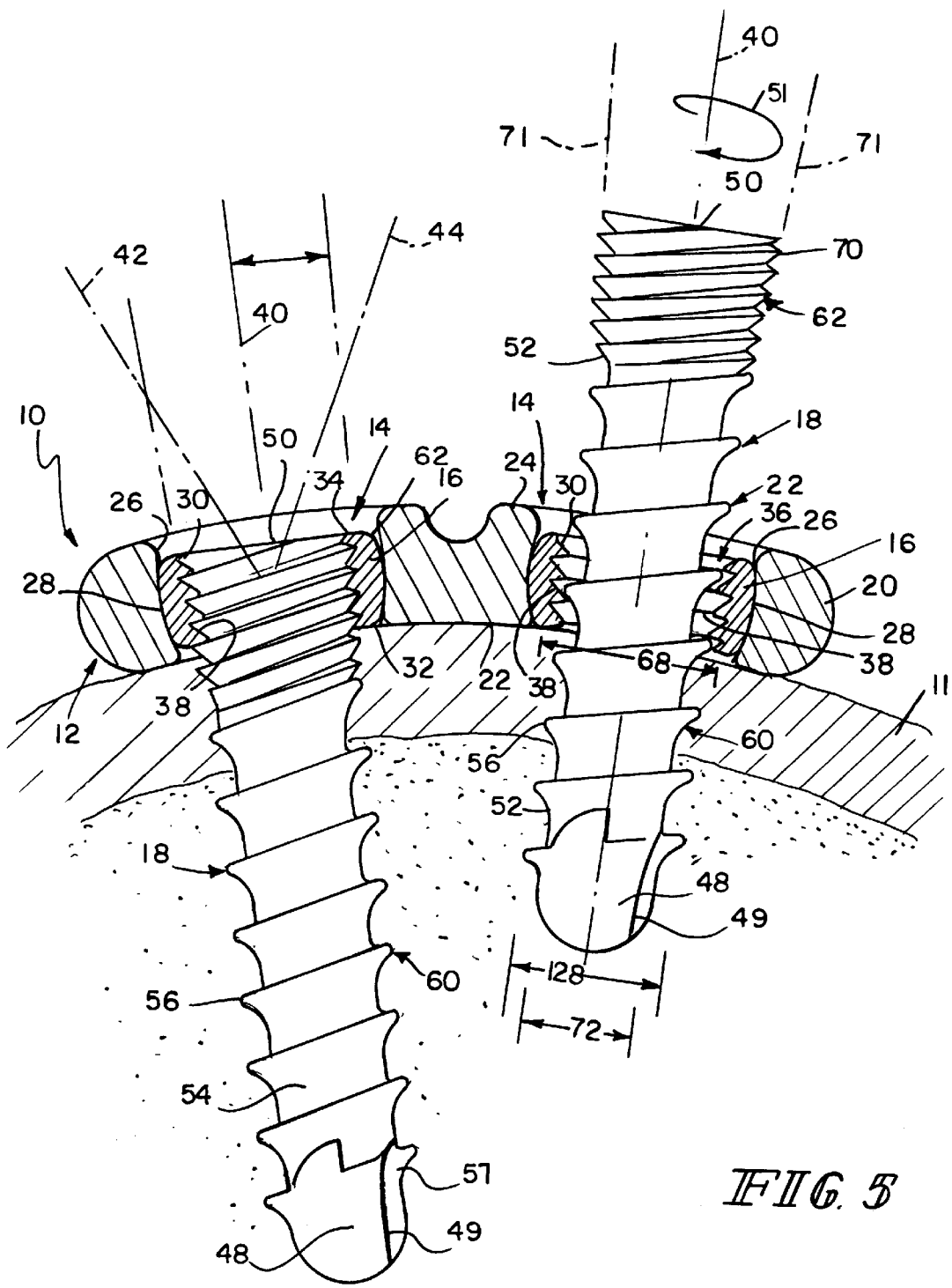
FIG. 5 is a cross section taken along lines 5—5 of FIG. 1 during attachment of the locking apparatus on the vertebrae, showing each thread-through bone screw including a single lead and multiple lead that tapers in a radially outward direction from the single lead and showing the multiple lead of a first bone screw frictionally coupling the bushing to the locking plate and showing the single lead of a second bone screw engaging the threads positioned within the passageway of the bushing.

As shown in FIGS. 3 and 5, bushing 16 includes a first end 32 configured to lie adjacent proximal surface 22 and an opposite second end 34 positioned to lie adjacent distal surface 24 of locking plate 12. In addition, bushing 16 includes a spherical-shaped radially exterior surface 28 extending between first and second ends 32, 34 and an opposite radially interior surface 30. While bushing 16 is illustrated with a spherically-shaped and smooth exterior surface 28, it is understood that exterior surface 28 may be formed in a variety of rounded shapes and sizes to cooperate with internal wall 26 of locking plate 12.

Figure 4:
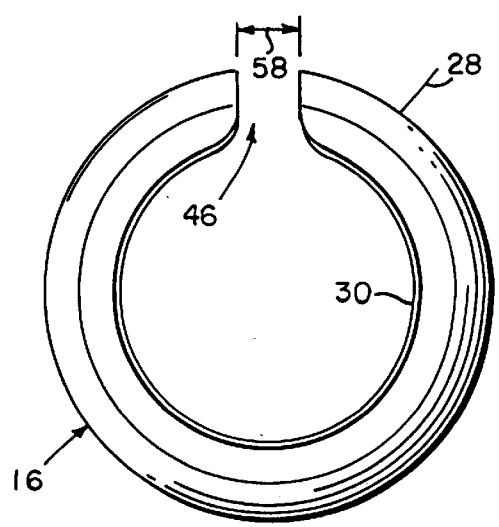
FIG. 4 is a top view of the bushing of FIG. 3 showing the bushing including a slot therethrough and showing the slot having a pre-determined dimension prior to extension of the bone screw through the passageway.

As shown in FIG. 3, radially interior surface 30 defines a passageway 36 that has an initial predetermined diameter 68 at second end 34 and that extends between first and second ends 32, 34 of bushing 16. Moreover, as shown in FIGS. 2 and 4, bushing 16 is formed to include a radial slot 46 that extends between exterior surface 28 and interior surface 30. As shown in FIG. 4, slot 46 has an initial predetermined -dimension 58. While slot 46 is illustrated and described, it is understood that bushing 16 may include multiple slots, cut-outs or otherwise be constructed to permit expansion of exterior surface 28. Radial expansion of bushing 16 expands slot 46 and presses exterior surface 28 against internal wall 26 for locking engagement between bushing 16 and locking plate 12.

Radially interior surface 30 of bushing 16 also includes threads 38 that extend radially inwardly into passageway 36 and define a diameter 72 adjacent to second end 34 therebetween. As shown in FIG. 3, threads 38 taper from second end 34 toward first end 32, as shown by lines 39. Tapered threads 38 converge at an angle of about five degrees to about twenty degrees, more preferably about five degrees to about twelve degrees, and most preferably about six degrees.

In addition, threads 38 have a tread pitch that is a multiple lead, with leads that start about 120°. Illustratively, the tapered pitch is a triple lead, although it is understood that the thread pitch, number of leads, and spacing may vary in accordance with the present invention.

Referring now to FIG. 2, exterior surface 28 of bushing 16 is positioned to lie within plate hole 14 of body portion 20 and engages internal wall 26. In addition, exterior surface 28 is sized to permit angled rotation of bushing 16 within plate hole 14 along a plurality of axes, as shown for example by lines 40, 42, 44. See FIG. 5. Illustratively, bushing 16 may be rotated within plate hole 14 along a plurality of axes so long as passageway 36 extends unobstructed between proximal and distal surfaces 22, 24 of locking plate 12 to permit extension of bone screw 18 therethrough. Thus, bushing 16 movably rides in plate hole 14 to form subassembly 17. As shown in FIG. 2, locking plate 12 has six plate holes 14 and six bushings 16 ride in six bone holes 14 and rotate independently of one another. Beneficially, subassembly 17 couples bone screws 18 therein without additional loose attachment components, providing surgeons an easy to handle locking plate apparatus 10.

Bone screw 18 is formed to engage bushing 16 and to fix the relative positioning of bushing 16 in plate hole 14. It is understood that while one bone screw 18 will be described hereafter, the description applies to all bone screws 18. Bone screw 18 is sized for extension through passageway 36 of bushing 16 and for pressing exterior surface 28 against internal wall 26 of locking plate 12 to form a friction lock between bushing 16 and locking plate 12. As shown in FIG. 5, bone screw 18 includes a leading portion 48 sized for extension through passageway 36 and into bone 11, an opposite trailing portion 50, and a middle portion 52 positioned to lie between leading and trailing portions 48, 50. Illustratively, leading portion 48 includes a plurality of sharp cutting edges 49 for self-tapping and reliefs 51 spaced apart from one another.

Bone screw 18 also includes an outer surface 54 and threads 56 extending about outer surface 54. Threads 56 have a thread pitch that is single lead 60 between leading and trailing portions 48, 50. Bone screw 18 also has thread pitch that is multiple lead 62 adjacent trailing portion 50. Simply, bone screw 18 includes a single lead 60 from tip to top with additional leads 62 being started within middle 52 toward trailing portion 50. Bone screw 18 is constructed of titanium alloy, although it is understood that bone screw 18 may be constructed of titanium, stainless steel, or any number of a wide variety of materials possessing the mechanical properties suitable for attachment with bone.

As shown in FIG. 5, single lead 60 adjacent to leading portion 48 engages threads 38 of bushing 16 prior to engaging bone 11. Threads 56 of single lead 60 have a diameter, as shown by arrow 68, that is greater than diameter 72 of threads 38. Thus, threads 38 in bushing 16 will engage and guide single lead 60 during insertion of bone screw 18 into bone 11. As shown in FIG. 5, trailing portion 50 of bone screw 18 has a tapered portion 70 that diverges, as shown by lines 71, away from leading portion 48. Illustratively, tapered portion diverges at an angle of about six degrees from leading portion 48. Tapered portion 70 is sized to engage interior surface 30 of bushing 16 and expand diameter 68 of passageway 36 so that dimension 58 of slot 46 increases and exterior surface 28 is pressed against internal wall 26 to form the friction lock between bushing 16 and locking plate 12. Illustratively, multiple lead 62 is positioned to lie on tapered portion 70. Thread pitch of multiple lead 62 has leads that start about 120°. It is understood that leads between leading and trailing portions 48, 50 may vary in pitch and number in accordance with the present invention. Although bone screw 18 is illustrated and described, it is understood that locking plate 12 may be coupled to bone 11 with a variety of attachment components. For example, leading portion 48 of bone screw 18 may instead be a plug or a porous coated spike, so long as leading portion 48 attaches to bone 11 and trailing portion 50 expands bushing 16 frictionally to lock bushing 16 in position in plate hole 14.

Figure 6:
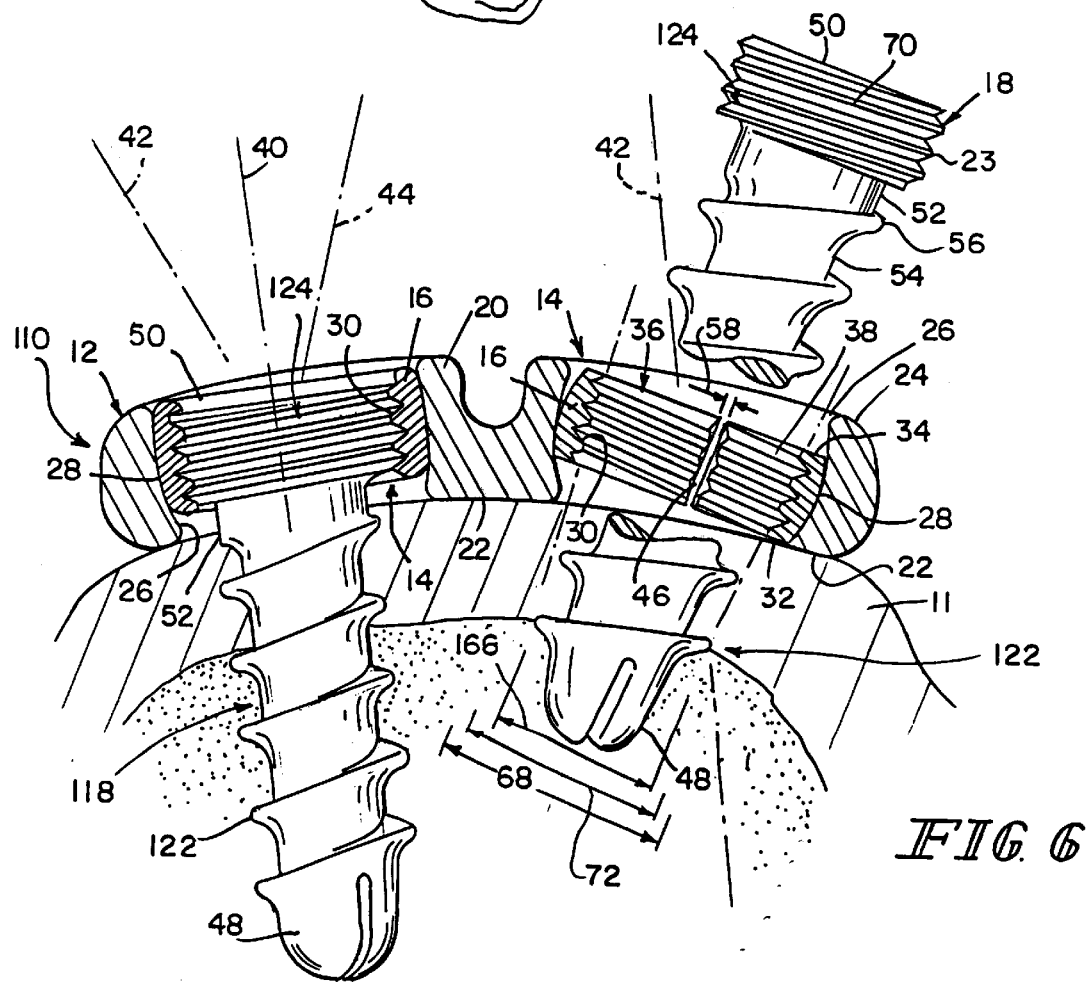
FIG. 6 is a view similar to FIG. 5 of an alternative embodiment of the present invention showing a locking apparatus including a locking plate, threaded bushings, and drop-in bone screws that each include a single lead sized for extension through the passageway spaced-apart from the threads of the bushing and a triple lead that presses the bushing against the locking plate frictionally to couple the bushing and the locking plate together.

In an alternative embodiment of the present invention, locking plate apparatus 110 is provided that include locking plate 12, bushings 16, and drop-in bone screws 118. See FIG. 6. To the extent that locking plate apparatus 110 is similar to locking plate apparatus 10 illustrated in FIGS. 1–5, like reference numerals will be used to denote like components. Referring to FIG. 6, bone screw 118 has a single lead 122 adjacent leading portion 48. Bone screw 118 also has a tapered multiple lead 124 adjacent to trailing portion 50. Multiple lead 124 has a diameter sized to spread bushing 16 to provide a fiiction lock with locking plate 12.

As shown in FIG. 6, single lead 122 of bone screw 118 has a diameter as shown by arrow 166 that is less than diameter 72 of threads 38 in bushing 16. Therefore, leading portion 48 of bone screw 118 is sized to slide through passageway 36 spaced apart from threads 38 of bushing 16. Multiple lead 124, however, is positioned on tapered portion 70 of bone screw 118 and engages threads 38 on bushing 16. Referring to FIG. 6, threads 38 of bushing 16 are configured to receive threads 123 of multiple lead 124 thereon and to guide insertion of tapered portion 70 into passageway 36.

Figure 7:
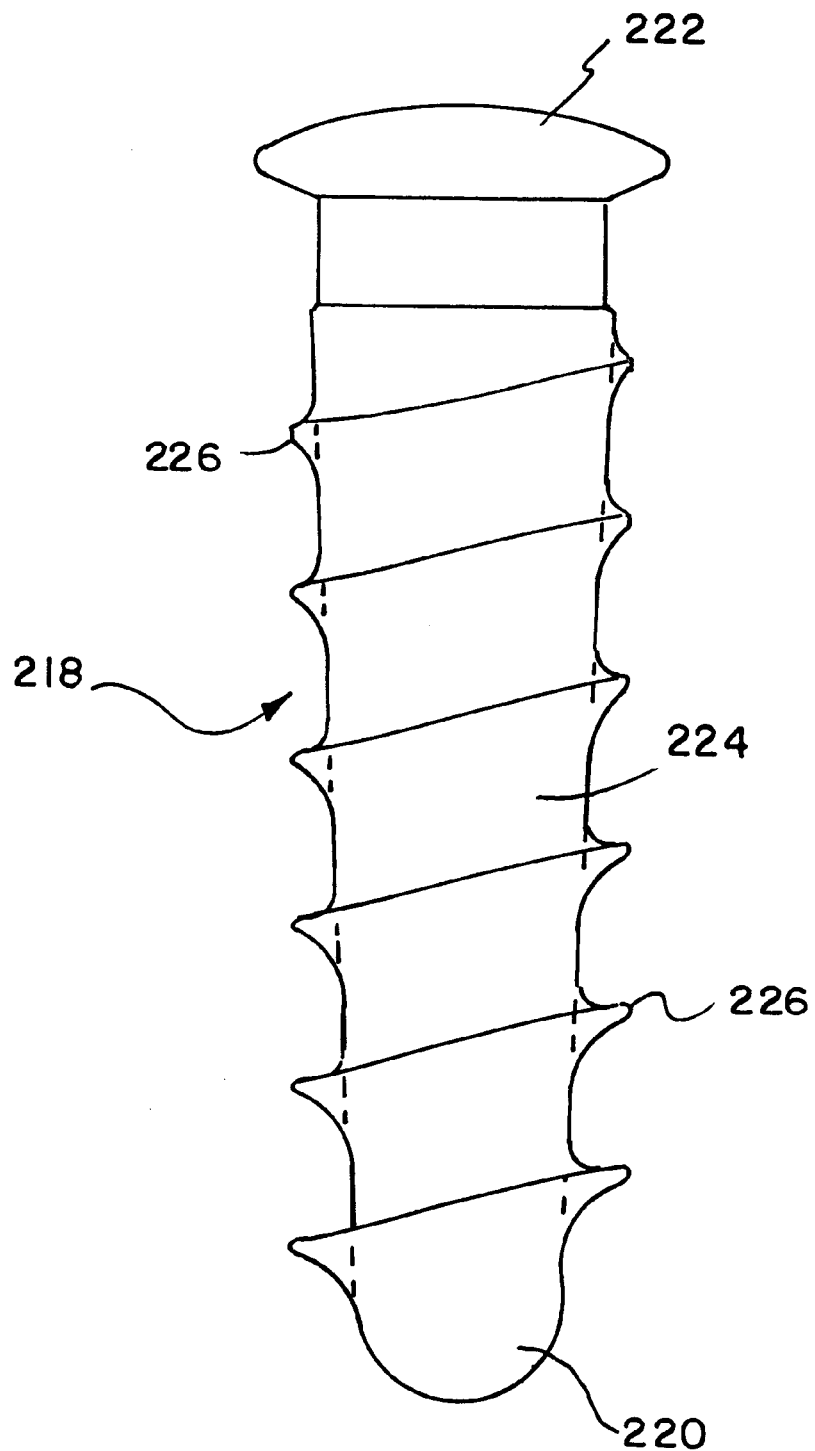
FIG. 7 is a side view of a graft screw, suitable for extending through graft holes in the locking plate.

A graft screw 218 is illustrated in FIG. 7 and is suitable for use with subassembly 17 in accordance with the present invention. Graft screw 218 is sized for extension through graft holes 25 and to stabilize the graft prior to fusion. Graft screw 218 includes a leading portion 220 and an opposite headed trailing portion 222. Graft screw 218 further includes an exterior wall 224 extending between leading and trailing portions 220, 222. Exterior wall 224 diverges from leading portion 220 toward trailing portion 222 at an angle of about six degrees. Moreover, threads 226 extend about exterior wall 224. As graft screw 218 extends into bone 11, exterior wall 224 becomes tighter and tighter against wall 23 until graft screw 218 snaps into place. While graft screw 28 is illustrated and described, it is understood that graft screws having a variety of shapes and sizes and other suitable attachment mechanisms may be used in accordance with the present invention to stabilize the graft.

Figure 8:
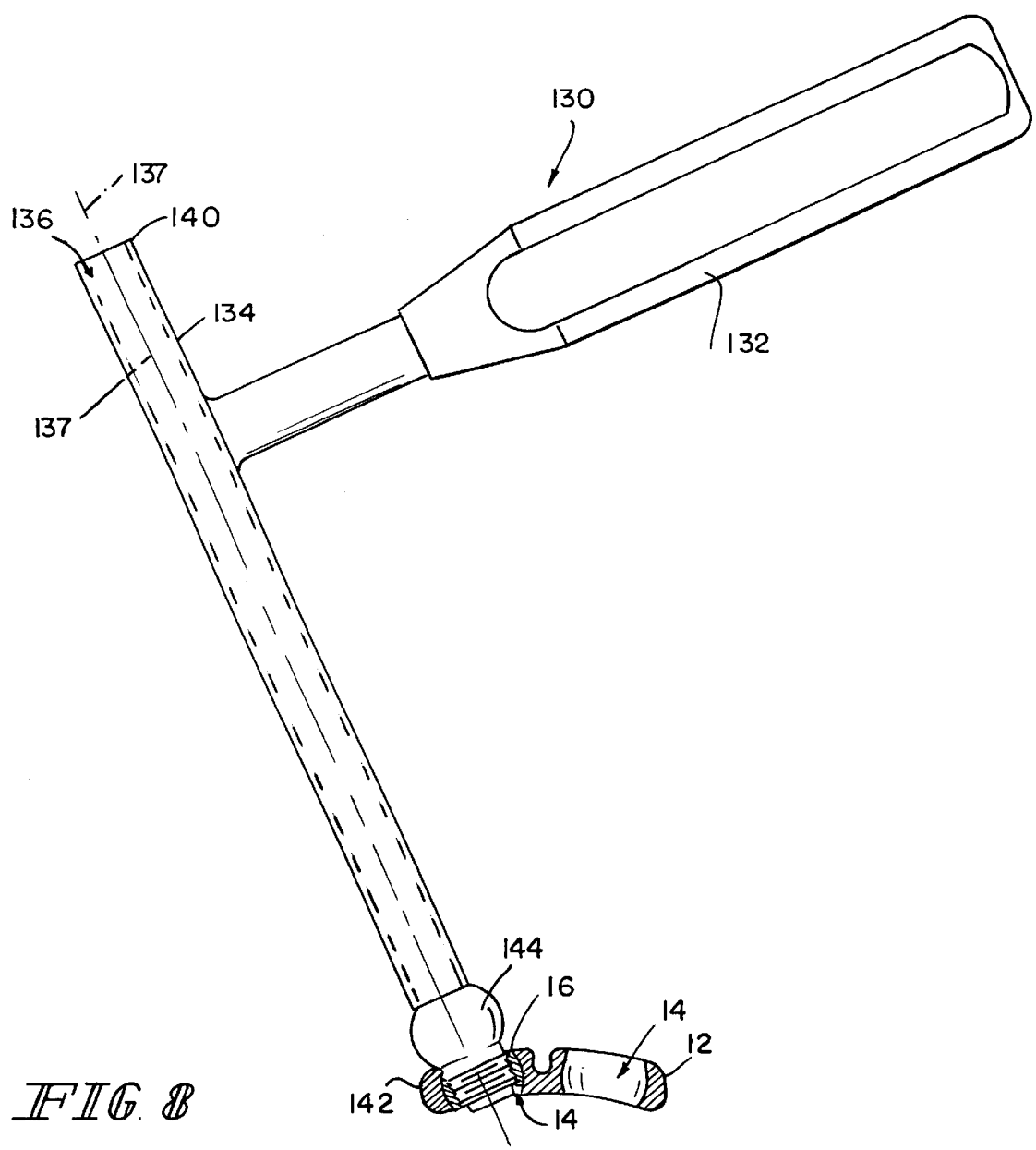
FIG. 8 is a cross-sectional view of the locking plate/bushing subassembly showing a drill guide extending into the passageway of one of the bushings to manipulate the positioning of the bushing in the plate hole relative to the bone.

To couple locking plate 12 to bone 11, the surgeon first positions subassembly 17 on bone 11 and selects a desirable angle in which to insert bone screw 18 into bone 11. A drill guide 130 is then inserted into passageway 36 of bushing 16 situated within plate hole 14 of locking plate 12. As shown in FIG. 8, drill guide 130 includes a handle portion 132 and an elongated guide portion 134 defining a plate hole 136 having axis 137 extending therethrough. Guide portion 134 includes an upper end 140 sized for insertion of a drill bit (not shown) therethrough and a lower end 142 having a stop portion 144 thereon. Stop portion 144 is sized to limit extension of guide portion 134 through plate hole 14 of locking plate 12. In addition, lower end 142 includes threads 146 that are sized to engage threads 38 on bushing 16. Therefore, to position drill guide 130 in passageway 36, lower end 142 is rotated relative to bushing 16 to couple threads 146 to threads 38 on bushing 16. While drill guide 130 is illustrated and described, it is understood that a drill tube or a wide variety of drill bit positioning mechanisms may be used to position bushing 16 in locking plate 12.

Once drill guide 130 engages bushing 16, the surgeon is free to rotate bushing 16 in plate hole 14 relative to vertebrae 11 along a plurality of axes 40, 42, 44 by moving handle portion 132 relative to locking plate 12. A desirable position of bushing 16 relative to locking plate 12 is selected by angling bushing 16 so that axis 137 of guide portion 132 and therefore passageway 36 of bushing 16 extends through a desirable segment of bone 11. Once a desirable position is selected, the surgeon uses a drill (not shown) to drill a pilot hole (not shown) into vertebrae 11 that is sized to receive leading portion 48 of bone screw 18. Drill guide 130 is then removed from passageway 36 of bushing 16.

Leading portion 48 of bone screw 18 is then inserted into passageway 36 of expandable bushing 16. Upon bone screw 18 entering passageway 36, threads 38 on bushing 16 receive threads 56 on leading portion 48 and guide leading portion 48 through passageway 36. The surgeon then rotates trailing portion 50 as shown by arrow 51 until leading portion 48 exits first end 32 of bushing 16 and extends into pilot hole (not shown). Once leading portion 48 has exited bushing 16, tapered portion 70 adjacent trailing portion 50 engages threads 38 on bushing 16. Continued rotation 51 in bushing 16 causes threads 38 on bushing 16 to receive threads 62 on tapered portion 70 and guide tapered portion 70 into passageway 36. Thus, tapered portion 70 expands diameter 68 of passageway 36 and presses exterior surface 28 of bushing 16 into a frictional locking engagement with internal wall 26 of locking plate 12. It is understood, that while drill guide 130 is illustrated and described, leading portion 48 of bone screw 18 may be formed to extend into bone 11 without a pilot hole.

In another embodiment of the present invention, leading portion 48 of bone screw 64 is inserted into passageway 36 of bushing 16. During insertion, leading portion 48 slides through passageway 36 so that threads 38 of bushing 16 are spaced apart from threads 56 of leading portion 48. Once leading portion 48 has "dropped into" pilot hole, tapered portion 70 adjacent to trailing portion 50 is rotated. Threads 38 on bushing 16 receive threads 123 on tapered portion 70 and guide tapered portion 70 into passageway 36. The surgeon continues to rotate bone screw 118 within bushing 16 until tapered portion 70 expands diameter 68 of passageway 36 and therefore presses spherical exterior surface 28 of bushing 16 into a frictional locking engagement with spherical internal wall 26 of locking plate 12.

Although the invention has been described in detail with reference to a preferred embodiment, variations and modifications exist within the scope and spirit of the invention as described and defined in the following claims.

What is claimed is:

1. A locking plate apparatus for engagement with a bone, the apparatus comprising:

a plate including a body portion and an internal wall defining a plate hole through the body portion, a bushing including a radially exterior surface and an opposite radially interior surface defining a passageway, the exterior surface being sized to permit polyaxial rotation of the bushing within the plate hole, and a bone screw including a leading portion sized for extension through the passageway and into the bone and an opposite trailing portion sized to press the bushing against the internal wall of the plate to form a friction lock between the bushing and the plate in a selected polyaxial position, the bone screw including threads having a single lead adjacent the leading portion and a multiple lead adjacent the trailing portion.

2. The locking plate apparatus of claim 1, wherein the single and multiple leads are formed for engagement with the bushing.

3. The locking plate apparatus of claim 1, wherein the interior surface of the bushing includes threads configured to receive the multiple lead of the bone screw.

4. The locking plate apparatus of claim 1, wherein the leading portion of the bone screw is sized for engagement with the interior surface of the bushing.

5. The locking plate apparatus of claim 1, wherein the plate is formed to include a plurality of holes therethrough, a plurality of bushings are movably coupled within the plate holes respectively, and a plurality of bone screws are provided for extension through passageways for selectively locking the position of the bushings relative to the plate.

6. A locking plate apparatus for engagement with a bone, the apparatus comprising:

a plate including a body portion and an internal wall defining a plate hole through the body portion, a bushing including a radially exterior surface and an opposite radially interior surface defining a passageway, the exterior surface being sized to permit polyaxial rotation of the bushing within the plate hole, and a bone screw including a leading portion sized for extension through the passageway and into the bone and an opposite trailing portion sized to press the bushing against the internal wall of the plate to form a friction lock between the bushing and the plate in a selected polyaxial position, the interior surface of the bushing including threads configured to receive at least a portion of the threads of the bone screw, the bushing is formed to include a slot that extends between the exterior surface and the interior surface and that has an initial pre-determined dimension, and the trailing portion has a tapered portion that diverges away from the leading portion and the tapered portion is sized to radially expand the exterior surface to form a friction lock between the bushing and the plate.

7. A locking plate apparatus for engagement with a bone, the apparatus comprising:

a plate including a body portion and an internal wall defining a plate hole through the body portion, a bushing including a radially exterior surface and an opposite radially interior surface defining a passageway, the exterior surface being sized to permit polyaxial rotation of the bushing within the plate hole, the bushing being formed to include a slot extending between the exterior surface and the interior surface and having an initial pre-determined dimension and an attachment component including a leading portion sized for extension through the passageway and into the bone and an opposite trailing portion sized to press the bushing against the internal wall of the plate to form a friction lock between the bushing and the plate in a selected polyaxial position and the trailing portion having a tapered portion diverging away from the leading portion and the tapered portion being sized to radially expand the exterior surface to form a friction lock between the bushing and the plate, the interior surface of the bushing including threads and the tapered portion of the attachment component including threads configured to engage the threads of the bushing.

8. The locking plate apparatus of claim 7, wherein the attachment component is a bone screw.

9. The locking plate apparatus of claim 8, wherein
the interior surface of the bushing includes threads configured to receive at least a portion of the threads of the bone screw.

10. The locking plate apparatus of claim 9, wherein the bushing is formed to include a slot that extends between the exterior surface and the interior surface and that has an initial pre-determined dimension.

11. A locking plate apparatus for engagement with a bone, the apparatus comprising:

a plate including a body portion and an internal wall defining a plate hole through the body portion, a bushing including a radially exterior surface and an opposite radially interior surface defining a passageway, the exterior surface being sized to permit polyaxial rotation of the bushing within the plate hole, the bushing being formed to include a slot extending between the exterior surface and the interior surface and having an initial pre-determined dimension and an attachment component including a leading portion sized for extension through the passageway and into the bone and an opposite trailing portion sized to press the bushing against the internal wall of the plate to form a friction lock between the bushing and the plate in a selected polyaxial position, and the trailing portion has a tapered portion diverging away from the leading portion and the tapered portion being sized to radially expand the exterior surface to form a friction lock between the bushing and the plate, the interior surface of the bushing includes threads and the attachment component is a bone screw with threads formed for engagement with the threads of the bushing.

12. A locking plate apparatus suitable for attachment with a bone, the apparatus comprising:

a plate being formed to include a distal surface, a proximal surface configured for engagement with the bone, and an internal wall defining a plate hole extending between the distal and proximal surfaces, a bushing including a radially exterior surface and an opposite interior surface defining a passageway, the exterior surface being sized for insertion into the plate hole of the plate and for engagement with the internal wall to couple movably the bushing to the plate, an attachment component sized for extension in the passageway, the attachment component including a leading portion and an opposite trailing portion, the trailing portion having a tapered portion that diverges away from the leading portion and is sized for pressing the bushing toward the internal wall of the plate to form a friction lock between the bushing and the plate, the passageway having a first pre-determined diameter and the tapered portion having a second diameter that is greater than the first pre-determined diameter, the tapered portion of the attachment component including threads that engage the interior surface of the bushing.

13. The locking plate apparatus of claim 12, wherein the leading portion has a third diameter that is less than the first pre-determined diameter.

14. The locking plate apparatus of claim 12, wherein the bushing is formed to include a radial slot between the exterior and interior surfaces and the passageway has an expanded diameter that is greater than the first pre-determined diameter when the tapered portion engages the interior surface of the bushing.

15. The locking plate apparatus of claim 12, wherein the interior surface of the bushing includes threads and the leading portion of the attachment component includes threads that engage the threads of the bushing.

16. A locking plate apparatus suitable for attachment with a bone, the apparatus comprising:

a plate being formed to include a distal surface, a proximal surface configured for engagement with the bone, and an internal wall defining a plate hole extending between the distal and proximal surfaces, a bushing including a radially exterior surface and an opposite interior surface defining a passageway, the exterior surface being sized for insertion into the plate hole of the plate and for engagement with the internal wall to couple movably the bushing to the plate, and an attachment component sized for extension in the passageway, the attachment component including a leading portion and an opposite trailing portion, the trailing portion having a tapered portion that diverges away from the leading portion and is sized for pressing the bushing toward the internal wall of the plate to form a friction lock between the bushing and the plate, the attachment component is a bone screw with threads including a single lead adjacent the leading portion and a multiple lead adjacent the trailing portion.

17. The locking plate apparatus of claim 16, wherein the passageway has a first pre-determined diameter and the tapered portion has a second diameter that is greater than the first pre-determined diameter.

18. The locking plate apparatus of claim 16, wherein the interior surface of the bushing includes threads to receive the multiple lead of the bone screw.

19. The locking plate apparatus of claim 18, wherein the multiple lead is positioned on the tapered portion.

20. The locking plate apparatus of claim 18, wherein the threads of the bushing are configured to receive at least a portion of the single lead of the bone screw.

21. The locking plate apparatus of claim 16, wherein the single lead is configured to guide rotation of the bushing within the plate hole about a plurality of axes.

22. A method for coupling two bone portions together, the method comprising the steps of:

providing a locking plate apparatus including a plate having a body portion and at least two plate holes through the body portion, a bushing movably coupled in each plate hole and having a radially exterior surface, an opposite interior surface, and first and second ends defining a passageway therebetween, and at an attachment component for each bushing sized for extension into the passageway, each attachment component including opposite leading and trailing portions, the interior surface of the bushing including threads and the attachment component is a bone screw having threads, positioning the body portion upon the bone portions so that the plate holes in the plate are situated over bone, rotating at least one bushing within the plate hole until the first and second ends of the bushing are aligned along an axis that extends through a pre-determined portion of the bone, inserting the leading portion of the attachment components into the respective passageway, and rotating the bone screw relative to the bushing so that the threads of the bushing lead the leading portion of the bone screw toward the bone driving the trailing portion of each attachment component through the respective passageway until the leading portion is positioned in the bone and the exterior surface of the bushing is pressed against the body portion to form a friction lock therebetween.

23. The method of claim 22, wherein the trailing portion of the bone screw includes a tapered portion diverging from the leading portion and the driving step includes rotating the bone screw relative to the bushing so that the threads of the bushing lead the tapered portion into the passageway and press the exterior surface of the bushing against the body portion of the plate.

24. A method for coupling two bone portions together, the method comprising the steps of:

providing a locking plate apparatus including a plate having a body portion and at least two plate holes through the body portion, a bushing movably coupled in each plate hole and having a radially exterior surface, an opposite interior surface, and first and second ends defining a passageway therebetween, and at an attachment component for each bushing sized for extension into the passageway, each attachment component including opposite leading and trailing portions, the interior surface of the bushing including threads thereon and the trailing portion of the attachment component including a tapered portion diverging from the leading portion, positioning the body portion upon the bone portions so that the plate holes in the plate are situated over bone, rotating at least one bushing within the plate hole until the first and second ends of the bushing are aligned along an axis that extends through a pre-determined portion of the bone, inserting the leading portion of the attachment components into the respective passageway, and driving the trailing portion of each attachment component through the respective passageway until the leading portion is positioned in the bone and the exterior surface of the bushing is pressed against the body portion to form a friction lock therebetween, and rotating the tapered portion relative to the bushing so that the threads of the bushing lead the tapered portion into the passageway and press the exterior surface of the bushing against the body portion of the plate.

25. The method of claim 24, wherein the leading portion of the attachment component is threaded and the inserting step includes sliding the leading portion through the passageway so that the threads of the bushing are spaced apart from the threads of the leading portion.

26. A bone fixation apparatus comprising a plate with a plate hole through the plate, a one piece bone fixation screw having a leading portion for extension through the plate hole and into a bone an opposite trailing portion, and an expansion bushing carried in the plate hole, said bushing being threaded to engage the screw and expandable by the trailing portion of the screw frictionally to lock in position in the plate hole.

27. A plate for bridging between and fixing the relative portions of bones, said plate having plate holes adjacent each bone, each plate hole carrying an expandable bushing therein for polyaxial movement selectively to position the axis of the bushing relative to the adjacent bone and a one piece bone screw, the bone screw including a leading portion for penetration into the bone and a trailing portion including threads and expanding the bushing against the plate to friction lock the bushing in a selected position in the plate.

28. A plate and screw apparatus for orthopaedic applications comprising a plate with a plurality of plate holes formed therein, each plate hole having an internal wall, a radially expandable bushing positioned in each plate hole to be held by said internal wall each bushing including an interior surface defining a passageway, and a screw for each plate hole, each screw having a leading portion for extension through the passageway and engaging a bone and a trailing portion including threads sized for engaging and expanding the bushing into locking engagement with the internal wall.

\* \* \* \* \*